United States Patent
Min et al.

(10) Patent No.: US 12,350,009 B2
(45) Date of Patent: Jul. 8, 2025

(54) ELECTRONIC DEVICE INCLUDING SENSOR MODULE

(71) Applicant: Samsung Electronics Co., Ltd., Suwon-si (KR)

(72) Inventors: Eungi Min, Suwon-si (KR); Inho Yun, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 281 days.

(21) Appl. No.: 17/972,763

(22) Filed: Oct. 25, 2022

(65) Prior Publication Data
US 2023/0131607 A1   Apr. 27, 2023

Related U.S. Application Data

(63) Continuation of application No. PCT/KR2022/016352, filed on Oct. 25, 2022.

(30) Foreign Application Priority Data

Oct. 25, 2021  (KR) .................. 10-2021-0142938
Mar. 11, 2022  (KR) .................. 10-2022-0030700

(51) Int. Cl.
*A61B 5/00*       (2006.01)
*G04G 21/02*     (2010.01)
*G01V 8/20*      (2006.01)

(52) U.S. Cl.
CPC .......... *A61B 5/0059* (2013.01); *A61B 5/6801* (2013.01); *G04G 21/025* (2013.01);
(Continued)

(58) Field of Classification Search
CPC ... A61B 5/0059; A61B 5/6801; A61B 5/2562; A61B 5/04; A61B 5/0238
See application file for complete search history.

(56) References Cited

U.S. PATENT DOCUMENTS

2003/0144584 A1   7/2003  Mendelson
2005/0002618 A1   1/2005  Miyamae et al.
(Continued)

FOREIGN PATENT DOCUMENTS

JP   2004-354532 A   12/2004
JP   2016-122004 A    7/2016
(Continued)

OTHER PUBLICATIONS

International Search Report dated Feb. 1, 2023, issued in International Application No. PCT/KR2022/016352.
(Continued)

*Primary Examiner* — Joel F Brutus
(74) *Attorney, Agent, or Firm* — Jefferson IP Law, LLP

(57) ABSTRACT

A wearable device is provided. The wearable device includes a housing including a transparent part, a circuit board disposed in the housing and including a first surface facing the transparent part and a second surface opposite to the first surface, a first integrated circuit (IC) layer disposed adjacent to the circuit board, a first sensor module, at least a part of which is disposed in the first IC layer, a second sensor module disposed adjacent to the first sensor module, and a second IC layer electrically connected to the first IC layer and the circuit board, and including a processor configured to process data acquired by the first sensor module and the second sensor module, wherein the circuit board, the first IC layer, and the second IC layer are stacked and disposed in a direction perpendicular to the first surface or the second surface of the circuit board.

17 Claims, 12 Drawing Sheets

(52) U.S. Cl.
CPC ... *A61B 2562/0238* (2013.01); *A61B 2562/04* (2013.01); *G01V 8/20* (2013.01)

(56) References Cited

U.S. PATENT DOCUMENTS

| | | | |
|---|---|---|---|
| 2008/0003842 | A1 | 1/2008 | Dabral et al. |
| 2008/0188724 | A1 | 8/2008 | Hwang et al. |
| 2018/0116532 | A1* | 5/2018 | Han .................. G06F 1/163 |
| 2018/0145205 | A1 | 5/2018 | Chen et al. |
| 2019/0274222 | A1 | 9/2019 | Kim et al. |
| 2019/0313916 | A1* | 10/2019 | Oh .................... A61B 5/021 |
| 2019/0391702 | A1 | 12/2019 | Jo et al. |
| 2020/0260972 | A1 | 8/2020 | Han et al. |
| 2020/0268263 | A1 | 8/2020 | Lee et al. |
| 2020/0323437 | A1 | 10/2020 | Lee et al. |
| 2020/0323489 | A1 | 10/2020 | Kim et al. |
| 2020/0401183 | A1 | 12/2020 | Von Badinski et al. |
| 2021/0007617 | A1 | 1/2021 | Kim et al. |
| 2021/0399563 | A1 | 12/2021 | Moon et al. |

FOREIGN PATENT DOCUMENTS

| | | |
|---|---|---|
| KR | 10-2008-0072158 A | 8/2008 |
| KR | 10-2019-0113552 A | 10/2019 |
| KR | 10-2020-0000129 A | 1/2020 |
| KR | 10-2020-0100487 A | 8/2020 |
| KR | 10-2020-0103350 A | 9/2020 |
| KR | 10-2020-0119501 A | 10/2020 |
| KR | 10-2020-0120407 A | 10/2020 |
| KR | 10-2021-0123551 A | 10/2021 |
| KR | 10-2502405 B1 | 2/2023 |
| WO | 2015/123606 A2 | 8/2015 |

OTHER PUBLICATIONS

Extended European Search Report dated Sep. 30, 2024; European Appln. No. 22887559.7-1113 / 4365686 PCT/KR2022016352.

* cited by examiner

ELECTRONIC DEVICE INCLUDING SENSOR MODULE

CROSS-REFERENCE TO RELATED APPLICATION(S)

This application is a continuation application, claiming priority under § 365(c), of an International application No. PCT/KR2022/016352, filed on Oct. 25, 2022, which is based on and claims the benefit of a Korean patent application number 10-2021-0142938, filed on Oct. 25, 2021, in the Korean Intellectual Property Office, and of a Korean patent application number 10-2022-0030700, filed on Mar. 11, 2022, in the Korean Intellectual Property Office, the disclosures of all of which are incorporated by reference herein in their entireties.

TECHNICAL FIELD

The disclosure relates to an electronic device including a sensor module.

BACKGROUND ART

An electronic device may refer to a device, such as home appliances, an electronic organizer, a portable multimedia player, a mobile communication terminal, a tablet PC, an image/sound device, a desktop/laptop computer, or a vehicle navigation device, for performing a specific function according to an installed program. For example, these electronic devices may output stored information as a sound or an image. As the degree of integration of an electronic device increases and high-speed and large-capacity wireless communication becomes common, various functions may have been installed in one electronic device, such as a mobile communication terminal, in recent years. For example, in addition to a communication function, an entertainment function such as a game, a multimedia function such as music/video playback, communication and security functions for mobile banking, or various functions such as schedule management or electronic wallets are being integrated in one electronic device. This electronic device is being miniaturized so as to be conveniently carried by a user. With the development of electronic and communication technologies, this electronic device is becoming smaller and lighter to the extent that the electronic device can be used without discomfort event when worn on the body.

Furthermore, an electronic device wearable on a physical body may be in continuous contact with a user's body for a considerable time. In addition, the electronic device may acquire various types of biometric information about the user and may provide the biometric information to the user. In order to provide more biometric information, it is increasingly demanded that a sensor module for acquiring the more biometric information should be disposed in the electronic device.

The above information is presented as background information only to assist with an understanding of the disclosure. No determination has been made, and no assertion is made, as to whether any of the above might be applicable as prior art with regard to the disclosure.

DETAILED DESCRIPTION OF THE INVENTION

Technical Problem

In a wearable electronic device, a sensor module for acquiring a user's biometric information may include a light emitter and a light receiver, and may analyze light reflected or scattered from the user. In arranging multiple sensor modules using light, the arrangement relationship between the multiple sensor modules needs to be adjusted in order to provide a miniaturized electronic device while reducing interference between the sensor modules.

Aspects of the disclosure are to address at least the above-mentioned problems and/or disadvantages and to provide at least the advantages described below. Accordingly, an aspect of the disclosure is to provide a structure in which multiple sensor modules are arranged adjacent to a processor configured to process data acquired from the sensor modules.

Another aspect of the disclosure is to provide a miniaturized electronic device using multiple optical sensor modules with reduced interference therebetween while being disposed adjacent to each other in the electronic device.

Additional aspects will be set forth in part in the description which follows and, in part, will be apparent from the description, or may be learned by practice of the present embodiments.

Technical Solution

In accordance with an aspect of the disclosure, a wearable device is provided. The wearable device includes a housing including a transparent part, a circuit board disposed in the housing and including a first surface facing the transparent part and a second surface opposite to the first surface, a first IC (integrated circuit) layer disposed on the circuit board, the first IC layer including a first sensor module and a second sensor module disposed adjacent to the first sensor module, and a second IC layer electrically connected to the first IC layer and the circuit board, and including a processor configured to process data acquired by the first sensor module and the second sensor module, wherein the first IC layer and the second IC layer are disposed adjacent to each other on the first surface or the second surface in a direction parallel to the longitudinal direction of the first surface or the second surface.

In accordance with another aspect of the disclosure, a wearable device is provided. The wearable device includes a housing including a transparent part, a circuit board disposed in the housing and including a first surface facing the transparent part and a second surface opposite to the first surface, a first IC layer disposed adjacent to the circuit board, a first sensor module, at least a part of which is disposed in the first IC layer, a second sensor module disposed adjacent to the first sensor module, and a second IC layer electrically connected to the first IC layer and the circuit board, and including a processor configured to process data acquired by the first sensor module and the second sensor module, wherein the circuit board, the first IC layer and the second IC layer are stacked and disposed in a direction perpendicular to the first surface or the second surface of the circuit board.

Advantageous Effects

Various embodiments of the disclosure may provide an electronic device miniaturized by stacking a first IC layer, in which at least a part of a sensor module is disposed, and a second IC layer for processing data acquired from the sensor module.

Various embodiments of the disclosure may provide an electronic device wherein a member for adjusting a light path is disposed near a first sensor module and a second sensor module, and thus interference between a first sensor module and a second sensor module are reduced.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF DRAWINGS

The above and other aspects, features, and advantages of certain embodiments of the disclosure will be more apparent from the following description taken in conjunction with the accompanying drawings, in which.

Throughout the drawings, it should be noted that like reference numbers are used to depict the same or similar elements, features, and structures.

MODE FOR CARRYING OUT THE INVENTION

The following description with reference to the accompanying drawings is provided to assist in a comprehensive understanding of various embodiments of the disclosure as defined by the claims and their equivalents. It includes various specific details to assist in that understanding, but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but are merely used by the inventor to enable a clear and consistent understanding of the disclosure. Accordingly, it should be apparent to those skilled in the art that the following description of various embodiments of the disclosure is provided for illustration purposes only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Figure 1:
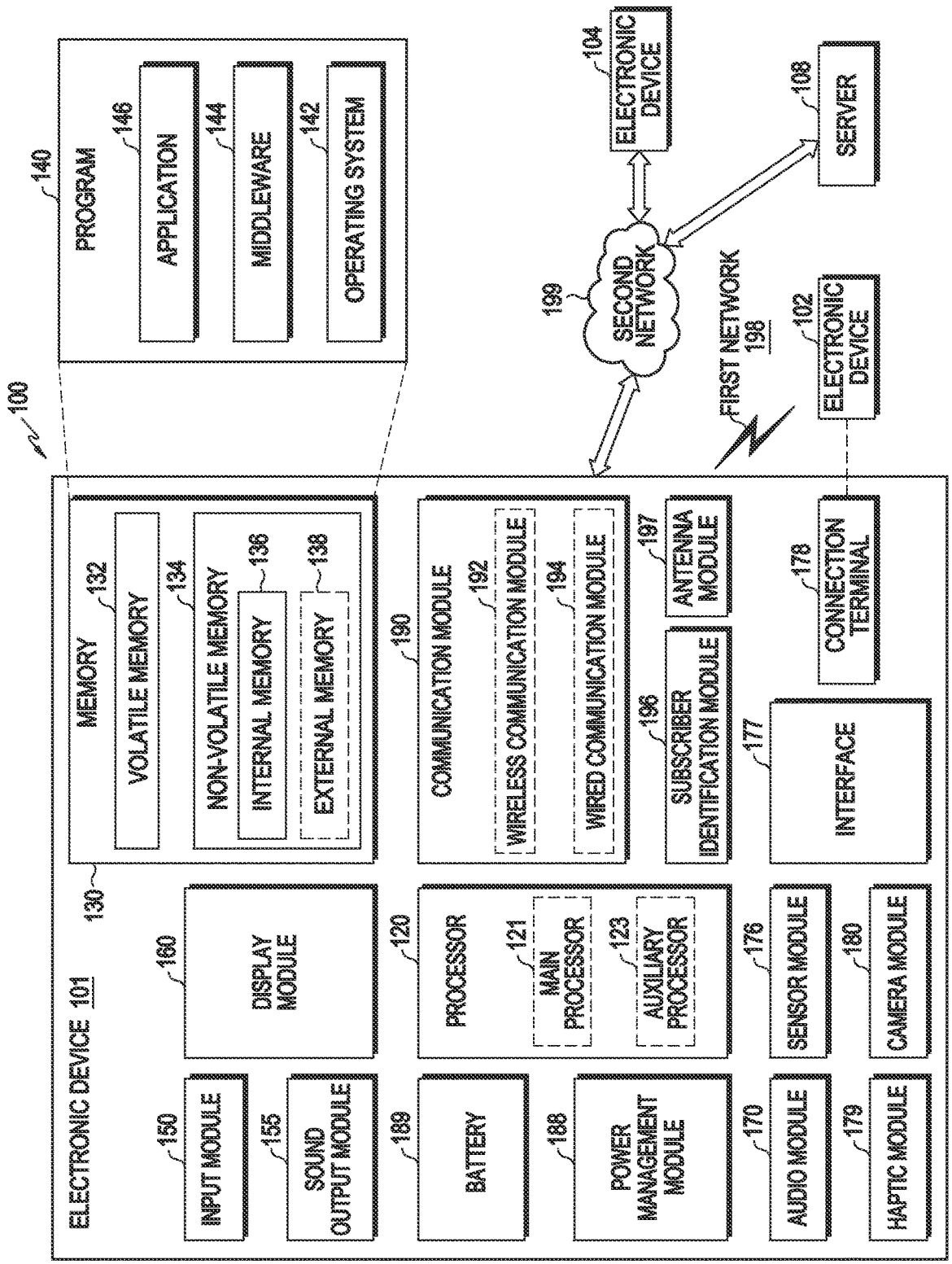
FIG. 1 shows an electronic device in a network environment according to an embodiment of the disclosure.

FIG. 1 is a block diagram illustrating an electronic device 101 in a network environment 100 according to an embodiment of the disclosure.

Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one of the components (e.g., the connecting terminal 178) may be omitted from the electronic device 101, or one or more other components may be added in the electronic device 101. In some embodiments, some of the components (e.g., the sensor module 176, the camera module 180, or the antenna module 197) may be implemented as a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be adapted to consume less power than the main processor 121, or to be specific to a specified function. The auxiliary processor 123 may be implemented as separate from, or as part of the main processor 121.

The auxiliary processor 123 may control, for example, at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active (e.g., executing an application) state. According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. An artificial intelligence model may be generated by machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134. The non-volatile memory 134 may include internal memory 136 and external memory 138.

The program 140 may be stored in the memory 130 as software, and may include, for example, an operating system (OS) 142, middleware 144, or an application 146.

The input module 150 may receive a command or data to be used by another component (e.g., the processor 120) of the electronic device 101, from the outside (e.g., a user) of the electronic device 101. The input module 150 may include, for example, a microphone, a mouse, a keyboard, a key (e.g., a button), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display module 160 may include, for example, a display, a hologram device, or a projector and control circuitry to control a corresponding one of the display, hologram device, and projector. According to an embodiment, the display module 160 may include a touch sensor adapted to detect a touch, or a pressure sensor adapted to measure the intensity of force incurred by the touch.

The audio module 170 may convert a sound into an electrical signal and vice versa. According to an embodiment, the audio module 170 may obtain the sound via the input module 150, or output the sound via the sound output module 155 or an external electronic device (e.g., an electronic device 102 (e.g., a speaker or a headphone)) directly or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, an HDMI connector, a USB connector, an SD card connector, or an audio connector (e.g., a headphone connector).

The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device 104 via the first network 198 (e.g., a short-range communication network, such as Bluetooth™, wireless-fidelity (Wi-Fi) direct, or infrared data association (IrDA)) or the second network 199 (e.g., a long-range communication network, such as a legacy cellular network, a 5G network, a next-generation communication network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify or authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device) of the electronic device 101. According to an embodiment, the antenna module 197 may include an antenna including a radiating element composed of a conductive material or a conductive pattern formed in or on a substrate (e.g., a printed circuit board (PCB)). According to an embodiment, the antenna module 197 may include a plurality of antennas (e.g., array antennas). In such a case, at least one antenna appropriate for a communication scheme used in the communication network, such as the first network 198 or the second network 199, may be selected, for example, by the communication module 190 from the plurality of antennas. The signal or the power may then be transmitted or received between the communication module 190 and the external electronic device via the selected at least one antenna. According to an embodiment, another component (e.g., a radio frequency integrated circuit (RFIC)) other than the radiating element may be additionally formed as part of the antenna module 197.

According to various embodiments, the antenna module 197 may form a mmWave antenna module. According to an embodiment, the mmWave antenna module may include a printed circuit board, an RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the external electronic devices 102 or 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or healthcare) based on 5G communication technology or IoT-related technology.

Figure 2:
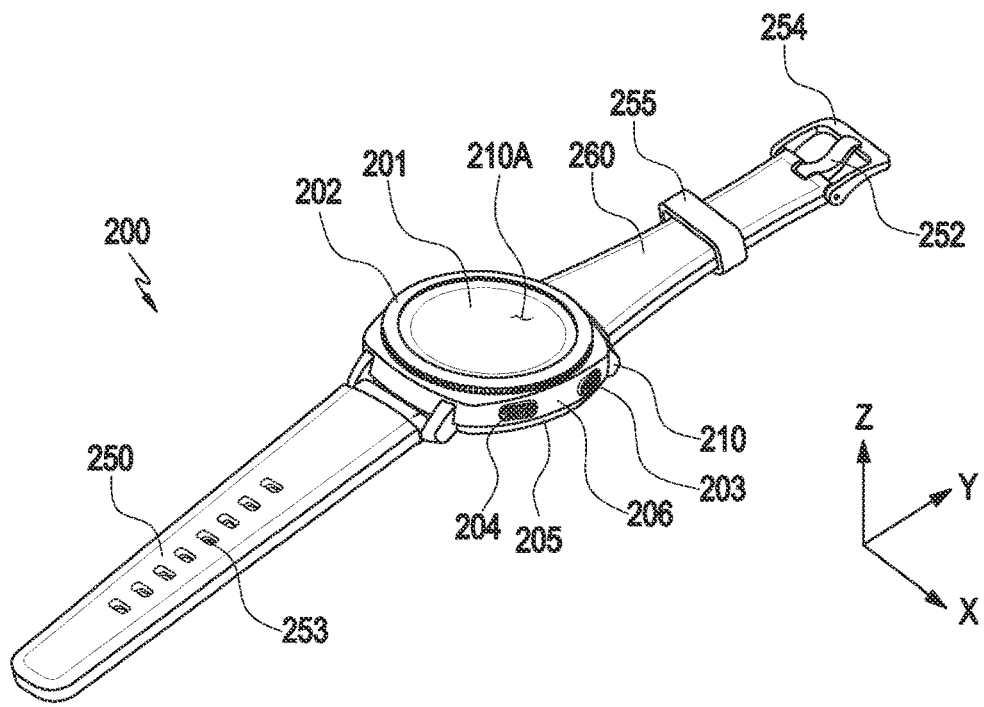
FIG. 2 is a front perspective view of an electronic device according to an embodiment of the disclosure.

FIG. 2 is a front perspective view of an electronic device according to an embodiment of the disclosure.

Figure 3:
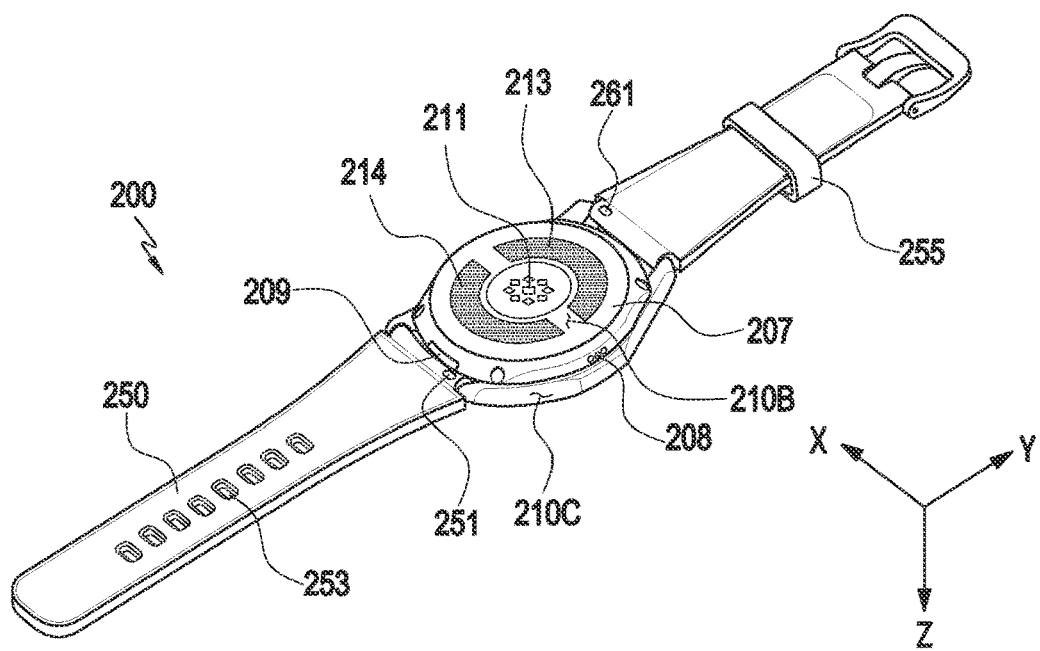
FIG. 3 is a rear perspective view of an electronic device according to an embodiment of the disclosure.

FIG. 3 is a rear perspective view of an electronic device according to an embodiment of the disclosure.

Referring to FIGS. 2 and 3, an electronic device 200 (e.g., the electronic device 101 in FIG. 1) according to an embodiment may include a housing 210 including a first surface (or a front surface) 210A, a second surface (or a rear surface) 210B, and a side surface 210C surrounding a space between the first surface 210A and the second surface 210B, and binding members 250 and 260, each of which is connected to at least a part of the housing 210 and is configured to detachably bind the electronic device 200 to a part (e.g., a wrist, an ankle, etc.) of a user's body. According to another embodiment of the disclosure (not shown), the housing may indicate a structure forming at least two of the first surface 210A, the second surface 210B, and the side surface 210C in FIG. 2. The first surface 210A may be formed of a front plate 201 (e.g., a polymer plate, or a glass plate including various coated layers), at least a part of which is substantially transparent. The second surface 210B may be formed of a rear plate 207 which is substantially opaque. The rear plate 207 may be formed of, for example, coated or colored glass, ceramic, polymer, metal (e.g., aluminum, stainless steel (STS), or magnesium), or a combination of at least two of the above-mentioned materials. The side surface 210C may be formed of a side bezel structure (or "a side member") 206 coupled to the front plate 201 and the rear plate 207 and containing metal and/or polymer. The rear plate 207 and the side bezel structure 206 may be integrally formed, and may contain an identical material (e.g., a metal material such as aluminum). The binding members 250 and 260 may be formed of various materials and in various forms. Integrated and multiple unit links may be formed to be movable with each other by using a woven material, leather, rubber, urethane, metal, ceramic, or a combination of at least two of the above-mentioned materials.

The electronic device 200 may include at least one among a display 330 (see FIG. 4), audio modules 205 and 208, a sensor module 211, key input devices 202, 203, and 204, and a connector hole 209. In the electronic device 200, at least one (e.g., the key input devices 202, 203, and 204, the connector hole 209, or the sensor module 211) of the elements may be omitted, or another element may be additionally included.

The display 330 (see FIG. 4) may be exposed through, for example, a considerable part of the front plate 201. The shape of display may correspond to the shape of the front plate 201, and may be various shapes such as a circular shape, an elliptical shape, or a polygonal shape. The display may be coupled to or disposed adjacent to a touch sensing circuit, a pressure sensor capable of measuring the strength (pressure) of a touch, and/or a fingerprint sensor.

The audio modules 205 and 208 may include a microphone hole 205 and a speaker hole 208. A microphone for acquiring an external sound may be disposed in the microphone hole 205. Multiple microphones may be disposed so as to sense the direction of a sound. The speaker hole 208 may be used as an external speaker or a call receiver. The speaker hole 208 and the microphone hole 205 may be implemented as one hole, or a speaker may be included without the speaker hole 208 (e.g., a piezo speaker).

The sensor module 211 may generate an electrical signal or a data value corresponding to the state of an operation inside the electronic device 200 or the state of an environment outside the electronic device 200. The sensor module 211 may include, for example, a biosensor module 211 (e.g., a heart rate monitor (HRM) sensor) disposed in the second surface 210B of the housing 210. The electronic device 200 may further include at least one of unillustrated sensor modules, such as, a gesture sensor, a gyro sensor, a barometric pressure sensor, a magnetic sensor, an acceleration sensor, a grip sensor, a color sensor, an infrared (IR) sensor, a biosensor, a temperature sensor, a humidity sensor, or an illumination sensor.

The sensor module 211 may include electrode regions 213 and 214 forming a part of the surface of the electronic device 200 and a biometric signal detection circuit (not shown) electrically connected to the electrode regions 213 and 214. For example, the electrode regions 213 and 214 may include a first electrode region 213 and a second electrode region 214, which are disposed on the second surface 210B of the housing 210. The sensor module 211 may be configured such that the electrode regions 213 and 214 acquire an electrical signal from a part of the user's body and the biometric signal detection circuit detects biometric information of the user, based on the electrical signal.

The key input devices 202, 203, and 204 may be disposed in the first surface 210A of the housing 210, and may include a wheel key 202 rotatable in at least one direction and/or side key buttons 203 and 204 disposed in the side surface 210C of the housing 210. The wheel key may have a shape corresponding to the shape of the front plate 201. According to another embodiment of the disclosure, the electronic device 200 may omit some or all of the above-mentioned key input devices 202, 203, and 204, and the key input devices 202, 203, and 204, which are not included, may be implemented in other forms, such as soft keys, on the display 330 (see FIG. 4). The connector hole 209 may receive a connector (e.g., a USB connector) for transmitting or receiving power and/or data to or from an external electronic device, and may include another connector hole (not shown) capable of receiving a connector for transmitting or receiving audio signals to or from an external electronic device. The electronic device 200 may further include, for example, a connector cover (not shown) for covering at least a part of the connector hole 209 and blocking introduction of outside foreign matter into the connector hole.

The binding members 250 and 260 may be detachably attached to at least a partial region of the housing 210 by using locking members 251 and 261. The binding members 250 and 260 may include at least one among a fixing member 252, a fixing member fastening hole 253, a band guide member 254, and a band fixing ring 255.

The fixing member 252 may be configured to fix the housing 210 and the binding members 250 and 260 to a part (e.g., a wrist, an ankle, etc.) of the user's body. The fixing member fastening hole 253 may correspond to the fixing member 252, and may fix the housing 210 and the binding members 250 and 260 to a part of the user's body. The band guide member 254 may be configured to restrict the range of movement of the fixing member 252 when the fixing member 252 is fastened to the fixing member fastening hole 253, so that the binding members 250 and 260 can be attached to the part of the user's body. The band fixing ring 255 may restrict the range of movement of the binding members 250 and 260 while the fixing member 252 is fastened to the fixing member fastening hole 253.

Figure 4:
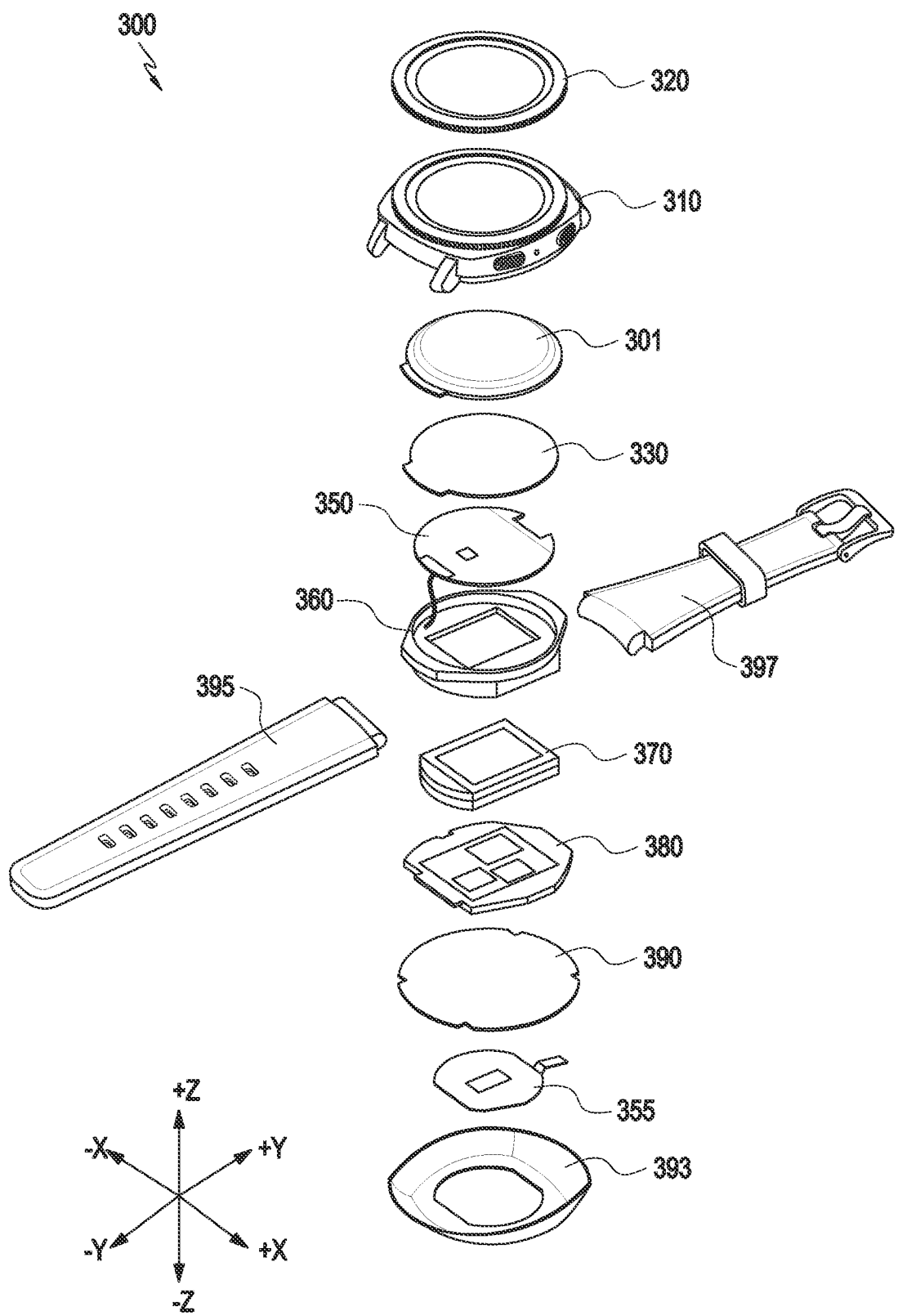
FIG. 4 is an exploded perspective view of an electronic device according to an embodiment of the disclosure.

FIG. 4 is an exploded perspective view of an electronic device according to an embodiment of the disclosure.

Referring to FIG. 4, an electronic device 300 (e.g., the electronic device 101 in FIG. 1 or the electronic device 200 in FIG. 2) may include a side bezel structure 310, a wheel key 320, a front plate 301, a display 330, a first antenna 350, a second antenna 355, a support member 360 (e.g., a bracket), a battery 370, a printed circuit board 380, a sealing member 390, a rear plate 393, and binding members 395 and 397. At least one of the elements of the electronic device 300 may be identical or similar to at least one of the elements of the electronic device 200 in FIG. 1 or 2, and a description thereof will be omitted below. The support member 360 may be disposed in the electronic device 300 and connected to the side bezel structure 310, or may be formed integrally with the side bezel structure 310. The support member 360 may be formed of, for example, a metal material and/or a nonmetal (e.g., polymer) material. The support member 360 may have one surface to which the display 330 is coupled, and the other surface to which the printed circuit board 380 is coupled. A processor, a memory, and/or an interface may be mounted on the printed circuit board 380. The processor may include at least one of, for example, a central processing unit, an application processor, a graphic processing unit (GPU), an application processor sensor processor, or a communication processor.

The memory may include, for example, a volatile memory or a nonvolatile memory. The interface may include, for example, a high-definition multimedia interface (HDMI), a universal serial bus (USB) interface, an SD card interface, and/or an audio interface. The interface may electrically or physically connect, for example, the electronic device 300 to an external electronic device, and may include a USB connector, an SD card/MMC connector, or an audio connector.

The battery 370 supplies power to at least one element of the electronic device 300, and may include, for example, a primary cell that cannot be recharged, a secondary cell that can be recharged, or a fuel cell. At least a part of the battery 370 may be disposed substantially on the same plane as, for example, the printed circuit board 380. The battery 370 may be integrally disposed in the electronic device 200, and may be disposed to be detachable/attachable from/to the electronic device 200.

The first antenna 350 may be disposed between the display 330 and the support member 360. The first antenna 350 may include, for example, a near-field communication (NFC) antenna, a wireless charging antenna, and/or a magnetic secure transmission (MST) antenna. The first antenna 350, for example, may perform short-range communication with an external device, may wirelessly transmit or receive power necessary for charging, and transmit a short-range communication signal or a magnetic-based signal including payment data. According to another embodiment of the disclosure, an antenna structure may be formed the side bezel structure 310 and/or a part of the support member 360 or a combination thereof The second antenna 355 may be disposed between the printed circuit board 380 and the rear plate 393. The second antenna 355 may include, for example, a near-field communication (NFC) antenna, a wireless charging antenna, and/or a magnetic secure transmission (MST) antenna. The second antenna 355, for example, may perform short-range communication with an external device, may wirelessly transmit or receive power necessary for charging, and transmit a short-range communication signal or a magnetic-based signal including payment data. In another embodiment, an antenna structure may be formed of the side bezel structure 310 and/or a part of the rear plate 393 or a combination thereof.

The sealing member 390 may be positioned between the side bezel structure 310 and the rear plate 393. The sealing member 390 may be configured to block moisture and foreign matter introduced from the outside into a space surrounded by the side bezel structure 310 and the rear plate 393.

The electronic device 300 (e.g., the electronic device 101 in FIG. 1) may include at least two sensor modules (e.g., the sensor module 211 in FIG. 2 or 3). In one example, as described above, the sensor modules may acquire biometric information of a user. The at least two sensor modules (e.g., the sensor module 211 in FIG. 2 or 3) may be disposed in a housing (e.g., the housing 210 in FIG. 2) while being electrically connected to a circuit board (e.g., the printed circuit board 380 in FIG. 4). To this end, the electronic device 300 may include a sensor arrangement structure (e.g., a sensor arrangement structure 700 in FIG. 7) in which at least two sensor modules are space-efficiently arranged in the housing (e.g., the housing 210 in FIG. 2).

In the following description of the disclosure, with reference to the drawings, a sensor arrangement structure (e.g., the sensor arrangement structure 700 in FIG. 7) according to various embodiments will be described. Furthermore, for convenience of description, the case in which multiple sensor modules (e.g., the sensor module 211 in FIG. 2) arranged in the sensor arrangement structure 700 are a PPG sensor and a spectral sensor (e.g., a glucose sensor) will be mainly described.

Figure 5:
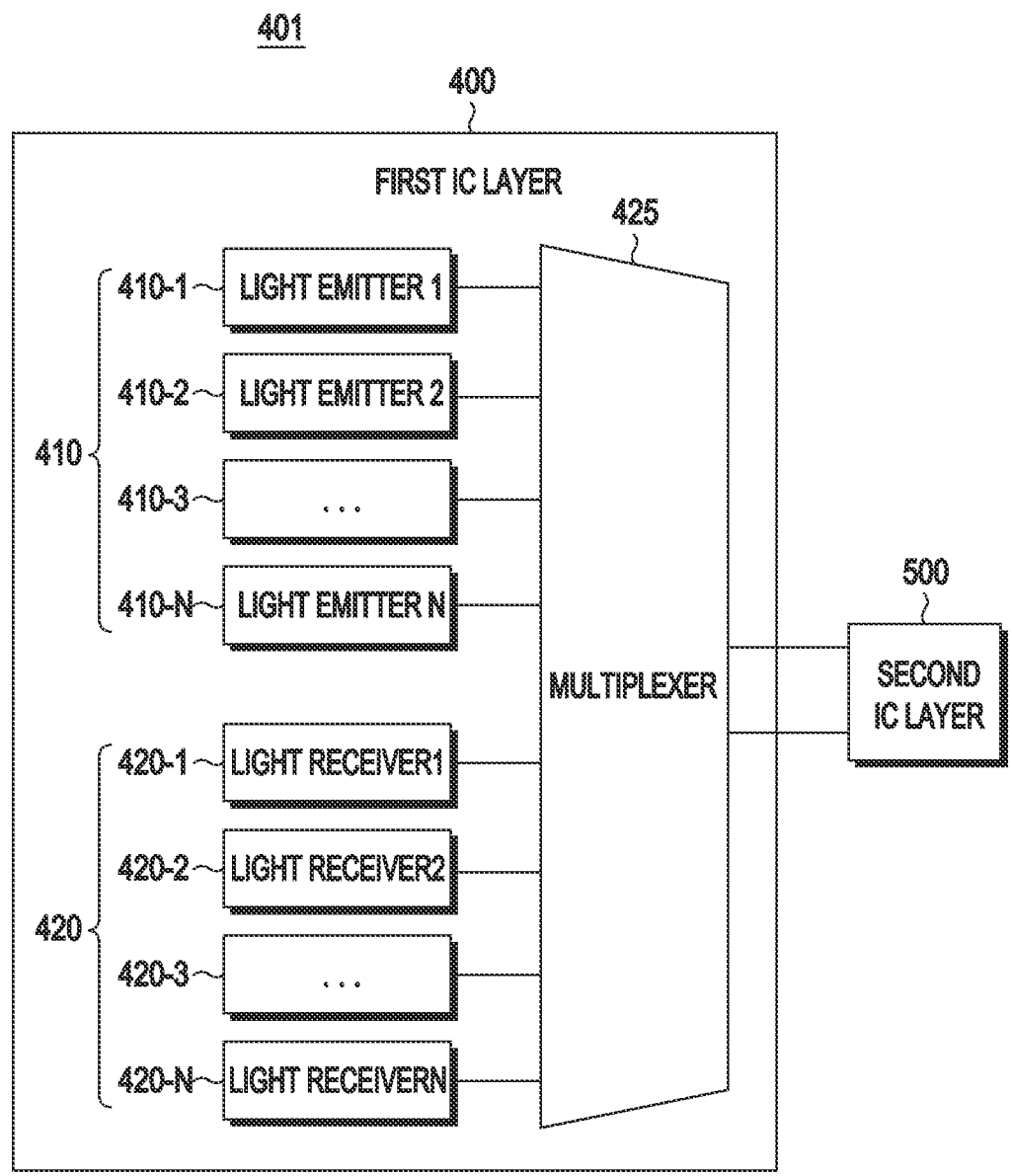
FIG. 5 is a block diagram showing a connection relationship between a first IC layer and a second IC layer according to an embodiment of the disclosure.

FIG. 5 is a block diagram showing a connection relationship between a first IC layer and a second IC layer according to an embodiment of the disclosure.

Referring to FIG. 5, an electronic device (e.g., the electronic device 101 in FIG. 1) may include a first sensor module 401 which includes a first IC(integrated circuit) layer 400 and a second IC layer 500 electrically connected to the first IC layer 400. The first sensor module 401 may include a spectral sensor module. For example, the first sensor module 401 may include an optical modulation module. As another example, the first sensor module 401 may include an electro-absorption modulator (EAM) or an electro-optic modulator (EOM). However, the disclosure is not limited thereto, and various types of spectral sensors or optical modulation modules may be used.

The first IC layer 400 may refer to a modulator for modulating a light-emitting signal band in a semiconductor-type spectral sensor. In the first IC layer 400, as described later, all or some of components constituting a second sensor module (e.g., a second sensor module (a PPG sensor) 761 in FIG. 8) may be arranged. In addition, in the first IC layer 400, some or all elements of various types of sensor modules included in the electronic device (e.g., the electronic device 101 in FIG. 1) may be arranged. For example, various types of sensor modules may include a gesture sensor, a gyro sensor, a barometric pressure sensor, a magnetic sensor, an acceleration sensor, a grip sensor, a proximity sensor, a color sensor, an infrared (IR) sensor, a biosensor, a temperature sensor, a humidity sensor, and/or an illuminance sensor.

The second IC layer 500 may refer to an ASIC layer for controlling the first IC layer 400, receiving data from the first IC layer 400, or transmitting data to the first IC layer 400.

The first IC layer 400 may include light emitters 410 and light receivers 420. The light emitters 410 may include first to Nth light emitters 410-1, 410-2, 410-3, . . . , 410-N). The light receivers 420 may include first to Nth light receivers 420-1, 420-2, 420-3, . . . , 420-N. The number of light emitters constituting the light emitters 410 may correspond to the number of light receivers constituting the light receivers 420. However, the disclosure is not limited thereto, and the numbers may be different from each other.

The multiple light emitters 410 and the multiple light receivers 420 may be electrically connected to the second IC layer 500 through a multiplexer 425. Thus, a connection structure between the first IC layer 400 and the second IC layer 500 may be simplified.

The second IC layer 500 may receive a signal for controlling the first IC layer 400 from a main processor (e.g., the main processor 121 in FIG. 1) to control the first IC layer 400. Furthermore, the second IC layer 500 may transfer an optical modulation signal, which the first IC layer 400 has acquired from the outside (e.g., a user), to the main processor (e.g., the main processor 121 in FIG. 1), and the main processor (e.g., the main processor 121 in FIG. 1) may analyze the optical modulation signal. Therefore, the electronic device (e.g., the electronic device 101 in FIG. 1) may provide a user with information related to the user's health.

Figure 6:
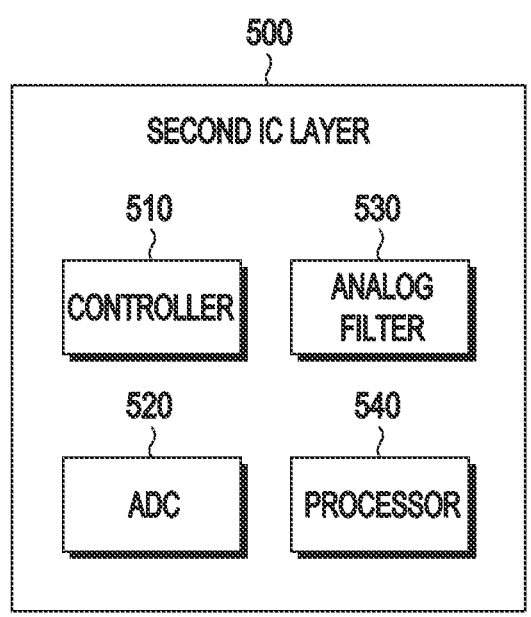
FIG. 6 is a block diagram showing elements of a second IC layer according to an embodiment of the disclosure.

FIG. 6 is a block diagram showing elements of a second IC layer according to an embodiment of the disclosure.

Referring to FIG. 6, the second IC layer 500 may include a controller 510, a converter (ADC) 520, a filter 530, and an auxiliary processor 540.

The controller 510 may control overall operations of a first sensor module (e.g., the first sensor module 401 in FIG. 5). For example, the controller 510 may control an operation of a light emitter (e.g., a first light emitter 774 in FIG. 8) included in the first sensor module. Furthermore, the controller 510 may control an operation of a light receiver (e.g., a first light receiver 772 in FIG. 8) included in the sensor module. The converter 520 may convert, to a digital signal, the amount of light (or an electrical signal corresponding to the light amount) acquired by the light receiver (e.g., the first light receiver 772 and/or a second light receiver 762 in FIG. 8) included in the sensor module. The analog filter 530 may reduce electrical noise in the second IC layer 500 and/or the above-mentioned first IC layer 400.

The auxiliary processor 540 may control over operations elements in the second IC layer 500. For example, the auxiliary processor 540 may acquire a digital signal about light from the converter 520, and may transfer the digital signal to a main processor (e.g., the main processor 121 in FIG. 1) in order to analyze the digital signal. In another example, the processor 540 may transmit, to the controller 510, a control signal for controlling the first sensor module 401.

Figure 7:
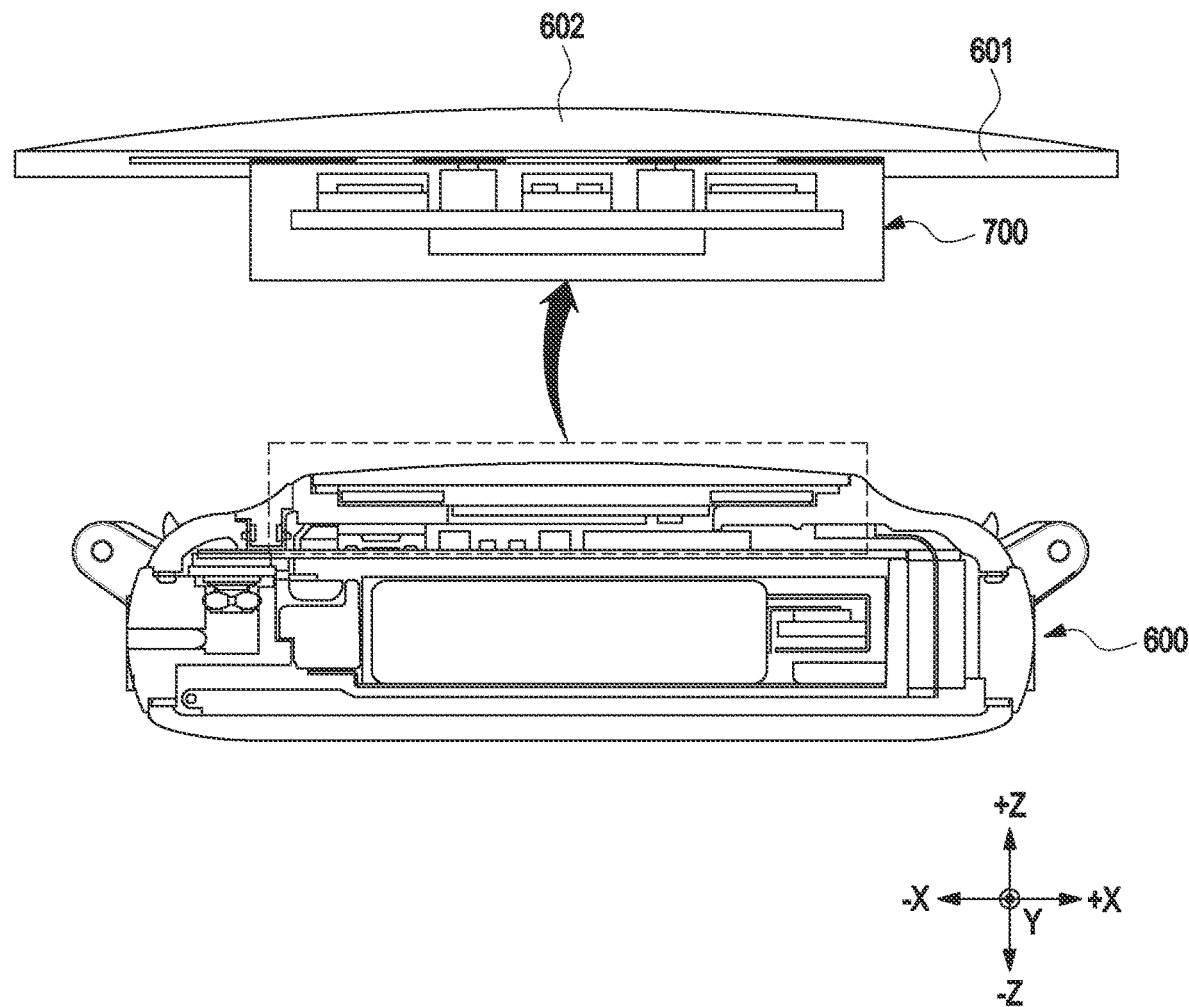
FIG. 7 is a cross-sectional view of an electronic device according to an embodiment of the disclosure.

FIG. 7 is a cross-sectional view of an electronic device according to an embodiment of the disclosure.

Referring to FIG. 7, an electronic device 600 may include a housing 601 and a sensor arrangement structure 700 in the housing 601. The electronic device 600 in FIG. 7 may be fully or partially identical or similar in configuration to the electronic device (e.g., the electronic device 200 in FIG. 2) in the above-mention embodiments.

The sensor arrangement structure 700 may be disposed in the housing 601. The housing 601 may include a transparent part 602. The transparent part 602 may be disposed on the housing 601 as a separate element, and may be formed integrally with the housing 601. For example, the transparent part 602 may be formed of glass or a plastic material. The sensor arrangement structure 700 may include a sensor using a light emitter and a light receiver. In this case, the sensor arrangement structure 700 may be disposed adjacent to the transparent part 602. For example, the sensor arrangement structure 700 may be disposed under the transparent part 602 to be optically connected to the outside of the electronic device 600.

Figure 8:
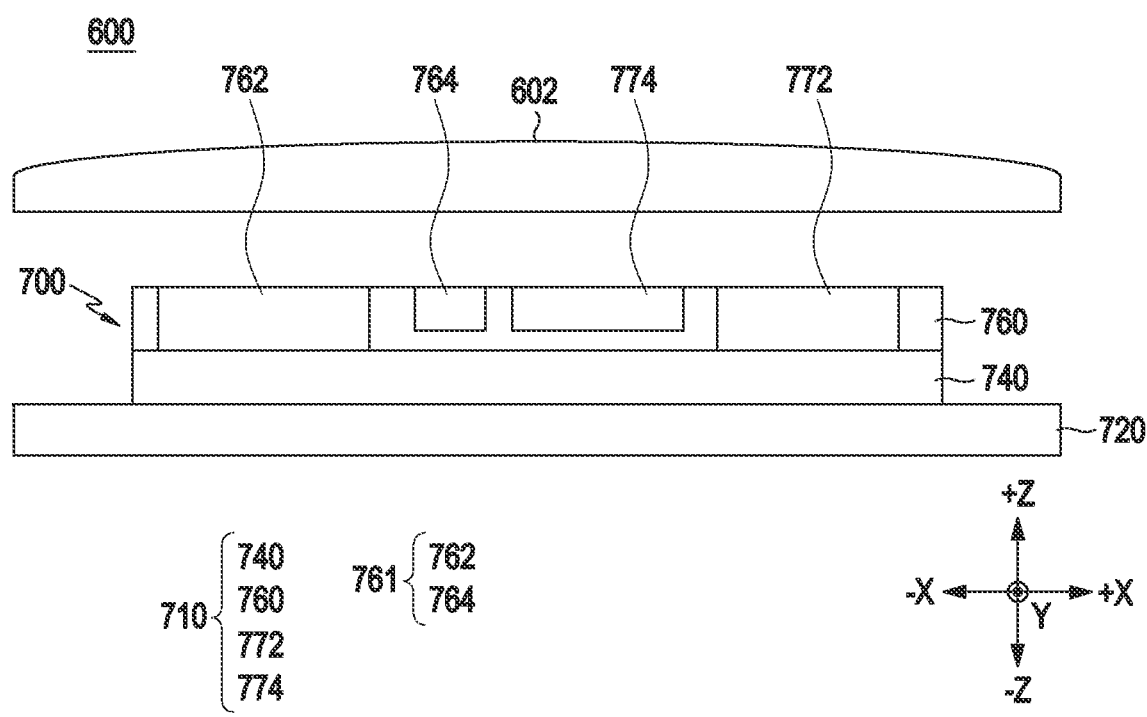
FIG. 8 shows an implementation example of a sensor arrangement structure according to an embodiment of the disclosure.

FIG. 8 shows an implementation example of a sensor arrangement structure according to an embodiment of the disclosure.

Referring to FIG. 8, the sensor arrangement structure 700 may include a circuit board 720, a second IC layer 740, and a first IC layer 760. The circuit board 720 in FIG. 8 may be fully or partially identical or similar in configuration to the printed circuit board 380 in FIG. 4. The description of the second IC layer 500 and the first IC layer 400 in FIGS. 5 and 6 may be applied to the second IC layer 740 and the first IC layer 760 in FIG. 8.

The first sensor module 710 may include the first IC layer 760, the second IC layer 740, a first light emitter 774, and a first light receiver 772. The first sensor module 710 in FIG. 8 may be fully or partially identical to the first sensor module 401 described in FIG. 5.

The second IC layer 740 may be disposed adjacent to the circuit board 720. Furthermore, the first IC layer 760 may be disposed adjacent to the second IC layer 740. For example, the second IC layer 740 may be disposed on the top portion ((+z-axis direction)) of the circuit board 720, and the first IC layer 760 may be disposed on the top portion (+z-axis direction) of the second IC layer 740. In another example, the circuit board 720 and the first IC layer 760 may be disposed to face each other with the second IC layer 740 interposed therebetween. The circuit board 720, the second IC layer 740 and the first IC layer 760 may be disposed so as to be in contact with each other for electrical connection, but may be disposed to be spaced a predetermined interval apart from each other. As described above, the second IC layer 740 may control an operation of the first IC layer 760, may analyze data acquired from the first IC layer 760, or may transfer the data to a main processor (e.g., the main processor 121 in FIG. 1). Since the first IC layer 760 and the second IC layer 740 are disposed adjacent to each other, an electrical connection therebetween may be facilitated, and the efficiency of a space in the electronic device 600 maybe improved.

All or a part of a second sensor module 761 may be disposed in the first IC layer 760. For example, the second sensor module 761 may be a PPG sensor. The second sensor module 761 may include a second light receiver 762 and a second light emitter 764. At least a portion of the second light emitter 764 and/or the second light receiver 762 may be disposed in the first IC layer 760.

The first light receiver 772 may receive light which is emitted from the first light emitter 774 and reflected or scattered by an object (e.g., a user) outside the electronic device 600. Furthermore, the second light receiver 762 may receive light which is emitted from the second light emitter 764 and reflected or scattered by an object (e.g., a user) outside the electronic device 600. The first IC layer 760 is disposed adjacent to the bottom portion (−z-axis direction) of the transparent part 602, and thus light emitted from the first light emitter 774 and the second light emitter 764 may be emitted to the outside through the transparent part 602, and the first light receiver 772 and the second light receiver 762 may receive light that is incident on the inside of the electronic device 600 through the transparent part 602.

The first sensor module 710 and the second sensor module 761 may be disposed adjacent to each other. According to an embodiment of the disclosure, the first light emitter 774 and the second light emitter 764 may be positioned in regions near the center of the first IC layer 760 in a horizontal direction (x-axis direction), and the first light receiver 772 and the second light receiver 762 may be positioned in peripheral regions of the first IC layer 760 in the horizontal direction (x-axis direction), respectively. According to another embodiment, the first light receiver 772 may be disposed at a first-side (+x-axis direction) periphery of the first IC layer 760 adjacent to the first light emitter 774, and the second light receiver 762 may be disposed a second-side (−x-axis direction) periphery of the first IC layer 760 adjacent to at the second light emitter 764. Accordingly, incidence of light (for example, light emitted from the first light emitter 774 and reflected by an external object), induced from the first light emitter 774, onto the second light receiver 762 may be reduced. Furthermore, similarly, incidence of light, induced from the second light emitter 764, onto the first light receiver 772 may be reduced.

Figure 9:
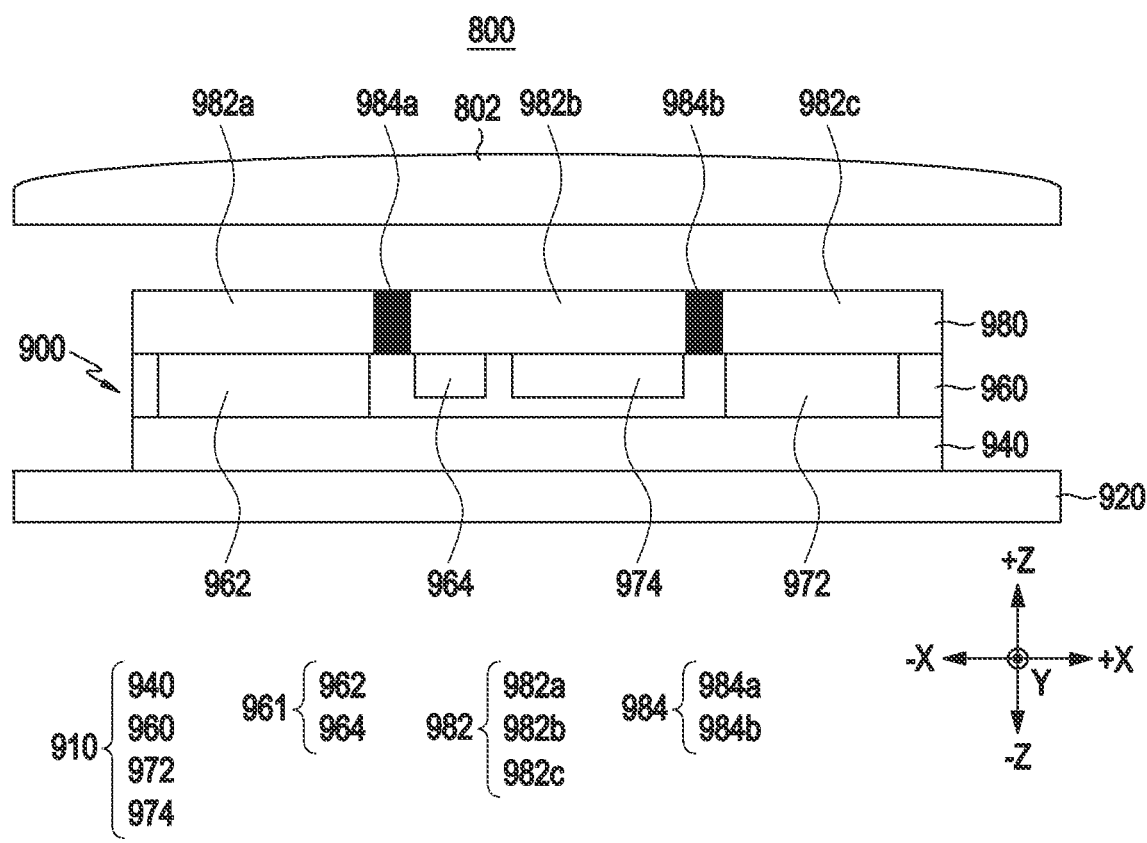
FIG. 9 shows an implementation example of a sensor arrangement structure according to an embodiment of the disclosure.

FIG. 9 shows an implementation example of a sensor arrangement structure according to an embodiment of the disclosure.

Referring to FIG. 9, a sensor arrangement structure 900 according to a second embodiment of the disclosure may include a circuit board 920, a second IC layer 940, a first IC layer 960, and a light transfer member 980. The description of the circuit board 720, the second IC layer 740, and the first IC layer 760 in FIG. 8 may be applied to a description of the circuit board 920, the second IC layer 940, and the first IC layer 960 in FIG. 9. An arrangement relationship between the circuit board 920, the second IC layer 940, and the first IC layer 960 may be identical or similar to the arrangement relationship between the circuit board 720, the second IC layer 740, and the first IC layer 760 in FIG. 8.

The light transfer member 980 may be disposed between a transparent part 802 and the first IC layer 960. For example, the light transfer member 980 may be disposed on the top (+z-axis direction) of the first IC layer 960 so as to provide a path for transferring light that is incident onto the first IC layer 960 through the transparent part 802 or is emitted from the first IC layer 960.

The light transfer member 980 may include a light-transmitting region 982 and a light blocking region 984. For example, the light transfer member 980 may be divided into multiple light-transmitting regions 982 by the light blocking region 984. According to an embodiment of the disclosure, the light-transmitting region 982 may include multiple light-transmitting regions. For example, the light-transmitting region 982 may include a first light-transmitting region 982a, a second light-transmitting region 982b, and a third light-transmitting region 982c. However, this is exemplary, and the number of the light-transmitting regions 982 may be adjusted based on the spirit of the disclosure. The light blocking region 984 may include a first light blocking region 984a dividing the first light-transmitting region 982a and the second light-transmitting region 982b, and a second light blocking region 984b dividing the second light-transmitting region 982b and the third light-transmitting region 982c.

The light transfer member 980 may be disposed on the top (+z-axis direction) of the first IC layer 960 such that the respective light-transmitting regions 982a, 982b, and 982c correspond to a first light receiver 972, a first light emitter 974, a second light receiver 962, and/or a second light emitter 964. The first light-transmitting region 982a may be disposed on the second light receiver 962, the second light-transmitting region 982b may be disposed on the first light emitter 974 and the second light emitter 964, and the third light-transmitting region 982c may be disposed on the first light receiver 972. Accordingly, light entering through the transparent part 802 may be incident on the second light receiver 962 through the first light-transmitting region 982a or may be incident on the first light receiver 972 through the third light-transmitting region 982c. Furthermore, light emitted from the first light emitter 974 and the second light emitter 964 may be transferred outside an electronic device 800 through the second light-transmitting region 982b.

According to an embodiment of the disclosure, with respect to the horizontal direction (the x-axis direction) of the electronic device 800, the light blocking region 984 may be disposed between the first and second light emitters 972 and 962 and the first and second light receivers 974 and 964. For example, the first light blocking region 984a may be disposed between the second light receiver 962 and the first light emitter 974 and/or the second light emitter 964 so as to reduce direct incidence of light from the first light emitter 974 and/or the second light emitter 964 onto the second light receiver 962. According to another embodiment of the disclosure, the second light blocking region 984b may be disposed between the first light receiver 972 and the first light emitter 974 and/or the second light emitter 964 so as to reduce direct incidence of light from the first light emitter 974 and/or the second light emitter 964 onto the first light receiver 972. The light blocking region 984 may divide multiple light-transmitting regions 982, thereby suppressing transferring of light to spaces between the respective light-transmitting regions 982. For example, the first light blocking region 984a may reduce mutual light transfer between the first light-transmitting region 982a and the second light-transmitting region 982b. Similarly, the second light blocking region 984b may reduce mutual light transfer between the second light-transmitting region 982b and the third light-transmitting region 982c. Therefore, interference between a first sensor module 910 and a second sensor module 961 may be reduced.

Figure 10A:
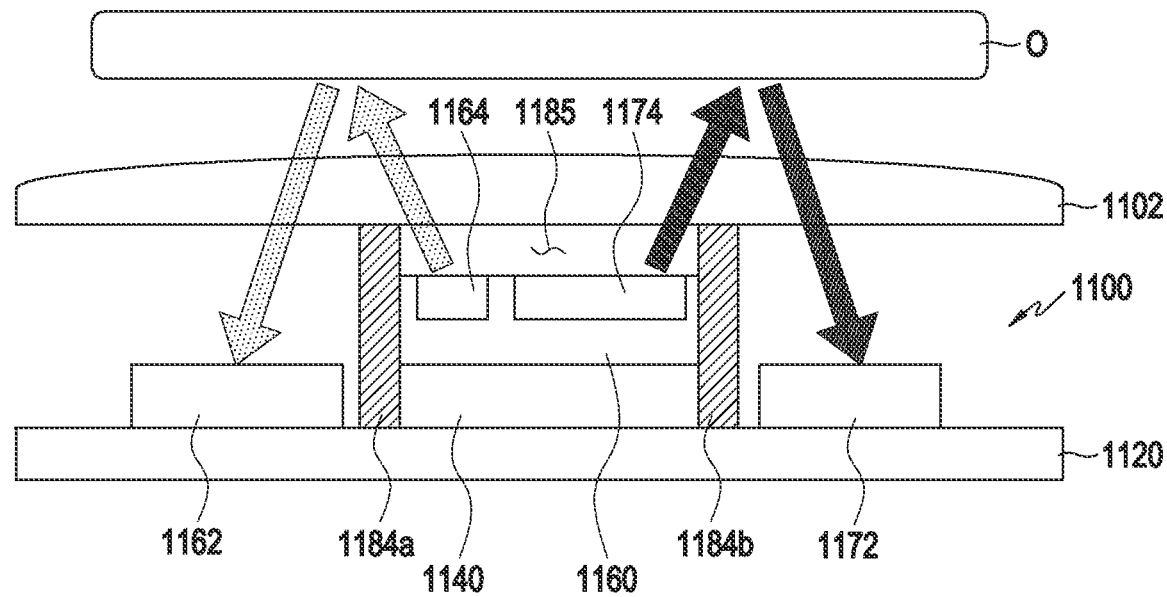
FIGS. 10A and 10B show implementation examples of a sensor arrangement structure according to various embodiments of the disclosure.
Figure 10B:
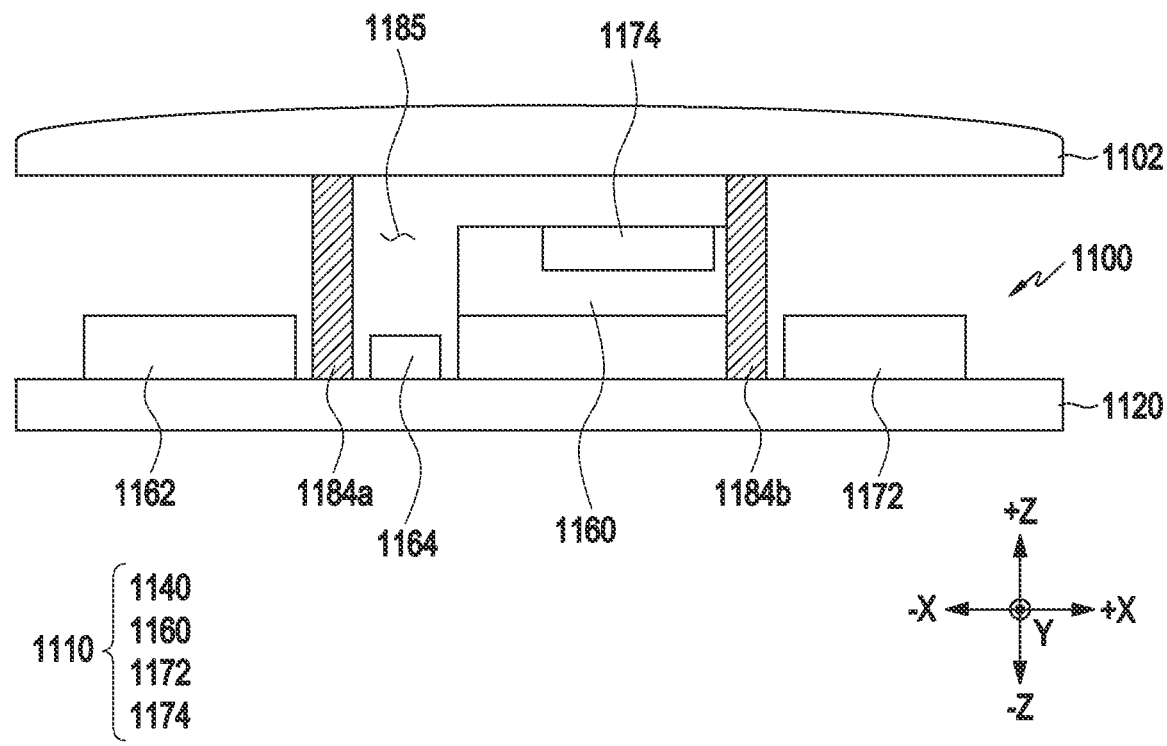

FIGS. 10A and 10B show implementation examples of a sensor arrangement structure according to various embodiments of the disclosure. FIG. 10A shows that a light emitter is integrated with a first IC layer. FIG. 10B shows that light emitter is disposed on each of a first IC layer or a circuit board.

Referring to FIGS. 10A and 10B, a sensor arrangement structure 1100 according to a third embodiment of the disclosure may include a circuit board 1120, a second IC layer 1140, a first IC layer 1160, and a light blocking member. The descriptions of the circuit boards 720 and 920, the second IC layers 740 and 940, and the first IC layer 760 and 960 in FIGS. 8 and 9 may be applied to a description of the circuit board 1120, the second IC layer 1140, and the first IC layer 1160 in FIGS. 10A and 10B.

At least one of the sensor modules 1110 may be disposed in the first IC layer 1160, and the others may be disposed on the circuit board 1120. For example, a first light receiver 1172 may be disposed on the circuit board 1120, and a first light emitter 1174 may be disposed on the first IC layer 1160. Similarly, a second light receiver 1162 may be disposed on the circuit board 1120, and a second light emitter 1164 may be disposed on the first IC layer 1160. Alternatively, referring to FIG. 10B, the first light emitter 1174 may be disposed on the circuit board 1120, and the second light emitter 1164 may be disposed on the first IC layer 1160, or vice versa (the second light emitter 1164 may be disposed on the circuit board 1120, and the first light emitter 1174 may be disposed on the first IC layer 1160).

The light blocking member may be disposed between the first and second light receivers 1172 and 1162 and the first and second light emitters 1174 and 1164. The light blocking member may include a first light blocking member 1184a and a second light blocking member 1184b. The second light blocking member 1184b may be disposed between the first light emitter 1174 and/or the second light emitter 1164 and the first light receiver 1172. Similarly, the first light blocking member 1184a may be disposed between the first light emitter 1174 and/or the second light emitter 1164 and the second light receiver 1162. The light blocking member may have a partition wall shape. The light blocking member may form a compartment region 1185. The compartment region 1185 may be a space between the first light blocking member 1184a and the second light blocking member 1184b. For example, as described above, the first IC layer 1160 and the second IC layer 1140 disposed in the upward/downward direction (the z-axis direction) may be disposed in the compartment region 1185. Furthermore, the first light receiver 1172 and the second light receiver 1162 may be disposed outside the compartment region 1185. In an embodiment, light emitted from the first light emitter 1174 may be reflected or scattered by an object O (e.g., a user's skin) outside a transparent part 1102, and then may be incident onto the first light receiver 1172. Furthermore, light emitted from the second light emitter 1164 may be reflected or scattered by the object O outside the transparent part 1102, and then may be incident onto the second light receiver 1162. Accordingly, similarly to the above-mentioned light blocking region (e.g., the light blocking region 984 in FIG. 9), direct incidence of light from the first light emitter 1174 and/or the second light emitter 1164 onto the first light receiver 1172 and/or the second light receiver 1162 may be reduced, and thus interference between a first sensor module 1110 and a second sensor module 1171 may be reduced.

Figure 11:
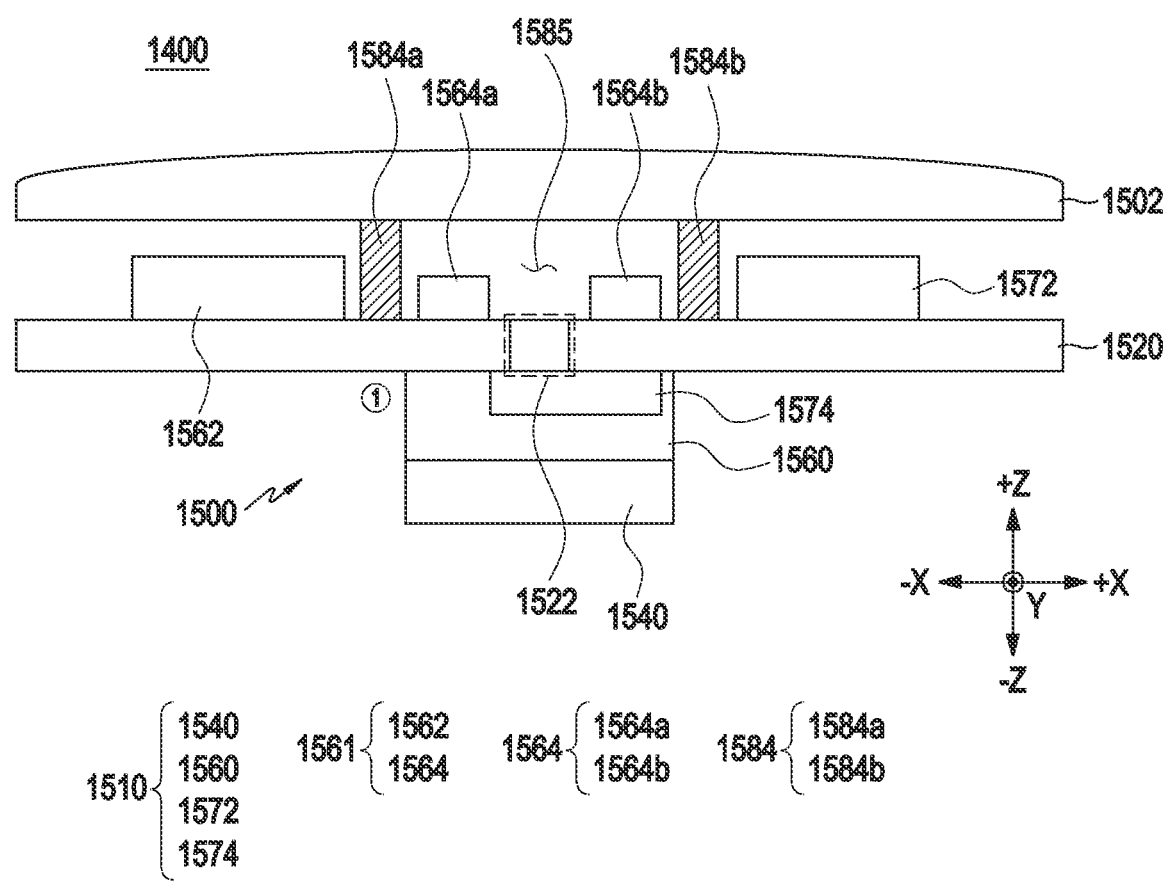
FIG. 11 shows an implementation example of a sensor arrangement structure according to an embodiments of the disclosure.

FIG. 11 shows an implementation example of a sensor arrangement structure according to an embodiment of the disclosure.

Referring to FIG. 11, a sensor arrangement structure 1500 according to a fourth embodiment of the disclosure may include a circuit board 1520, a second IC layer 1540, a first IC layer 1560, and a light blocking member 1584. The descriptions of the circuit boards 720, 920, and 1120, the second IC layers 740, 940, and 1140, and the first IC layers 760, 960, and 1160 in FIGS. 8, 9, 10A, and 10B may be applied to a description of the circuit board 1520, the second IC layer 1540 and the first IC layer 1560 in FIG. 11.

The circuit board 1520 may include an opening region 1522. The opening region 1522 may be formed through the circuit board 1520, and may provide a path through which light can pass.

At least one of a first sensor module 1510 and/or a second sensor module 1561 may be disposed on a first surface (the top surface or a +z-axis surface) of the circuit board 1520, and the others may be disposed on a second surface (the bottom surface or a −z-axis surface) of the circuit board 1520. In another example, at least one of the first sensor module 1510 and/or the second sensor module 1561 may be disposed to face the others with the circuit board 1520 interposed therebetween.

A first light receiver 1572, a second light 1564, and a second light receiver 1562 may be disposed on the first surface (the +z-axis surface) of the circuit board 1520, and the first IC layer 1560 including a second light emitter 1574 may be disposed on the second surface (the −z-axis surface) of the circuit board 1520. The first IC layer 1560 may be disposed on the second surface (the −z-axis surface) of the circuit board 1520 such that the first light emitter 1574 overlaps the opening region 1522. For example, the first light emitter 1574 may emit light toward the opening region 1522, and the emitted light may be transferred outside an electronic device 1400 through a transparent part 1502.

The first IC layer 1560 and the second IC layer 1540 may be stacked and disposed beneath the circuit board 1520 (the −z-axis direction). For example, as described above, the first IC layer 1560 may be disposed beneath the circuit board 1520 (the −z-axis direction) such that the first light emitter 1574 overlaps the opening region 1522, and the second IC layer 1540 may be disposed beneath the first IC layer 1560 (the −z-axis direction). The second IC layer 1540 and the first IC layer 1560 may be disposed to be in contact with each other. However, this is not essential, and the second IC layer 1540 and the first IC layer 1560 may be disposed to be spaced a predetermined distance apart from each other.

The second light emitter 1564 may be disposed on the first surface (the +z-axis surface) of the circuit board 1520 around the opening region 1522. According to an embodiment of the disclosure, multiple second light emitters 1564 (for example, the (2-1)th light emitter 1564a and the (2-2)th light emitter 1564b) may be provided. In FIG. 11, only two second light emitters 1564a and 1564b are illustrated, but it will be understood that more second light emitters may be disposed. The (2-1)th light emitter 1564a and the (2-2)th light emitter 1564b may be disposed to surround the opening region 1522. For example, a (2-1)th light emitter 1564a and the (2-2)th light emitter 1564b may be disposed at both sides of the opening region 1522, respectively. Furthermore, the (2-1)th light emitter 1564a and the (2-2)th light emitter 1564b may be disposed in a compartment region 1585. Accordingly, through the opening region 1522, light emitted from the first light emitter 1574 may be transferred, and light emitted from the second light emitter 1564 around the opening region 1522 may be transferred outside the electronic device 1400, whereby interference between the second light emitter 1564 and the first light emitter 1574 may be reduced.

In the illustrated embodiment, the description of the arrangement of the light blocking member 1184, made above with reference to FIGS. 10A and 10B, may be fully or partially applied to the arrangement of the light blocking member 1584, and thus a redundant description will be omitted. At least one of the second light emitters 1564 may be disposed between the light blocking member 1584 and the opening region 1522 in the horizontal direction (the +x-axis direction) of the electronic device 1400. For example, the (2-1)th light emitter 1564a may be disposed between a first light blocking member 1584a and the opening region 1522, and the (2-2)th light emitter 1564b may be disposed between a second light blocking member 1584b and the opening region 1522. Accordingly, direct incidence of light, emitted from the first light emitter 1574 and/or the second light emitter 1564, onto the first light receiver 1572 and/or the second light receiver 1562 may be reduced.

Figure 12A:
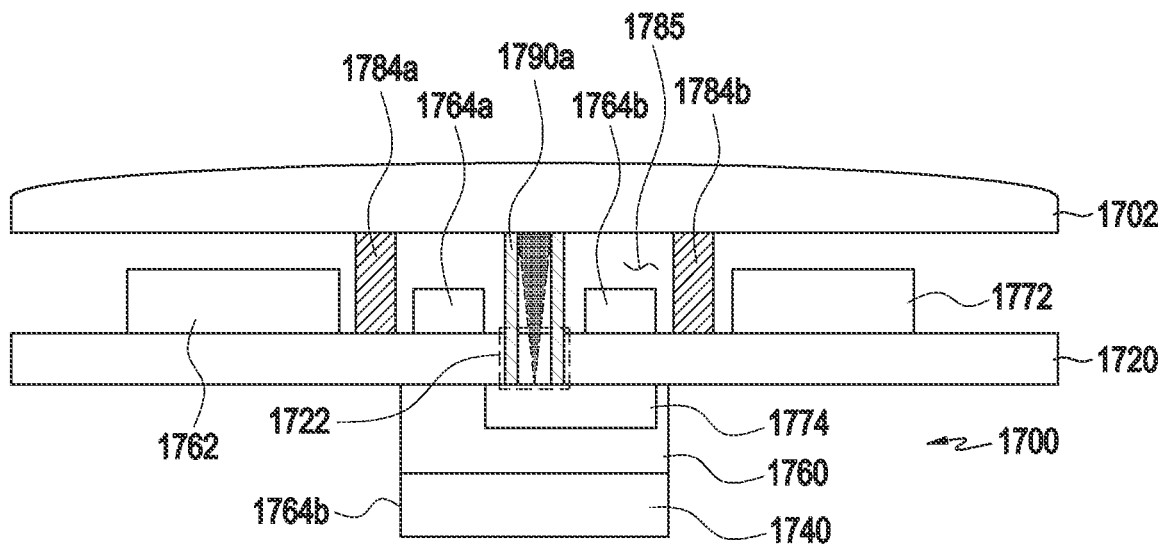
FIGS. 12A and 12B show implementation examples of a sensor arrangement structure according to various embodiments of the disclosure.
Figure 12B:
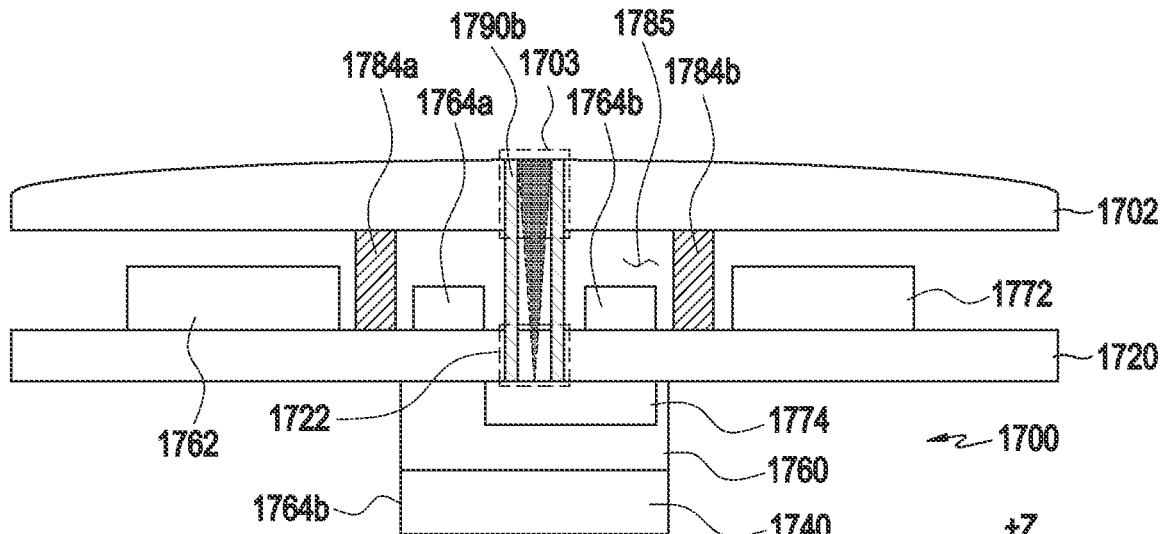
Figure 12B:
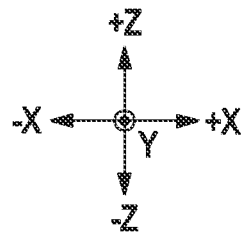

FIGS. 12A and 12B show implementation examples of a sensor arrangement structure according to various embodiments of the disclosure. FIG. 12A shows one implementation example of a light path member. FIG. 12B shows another implementation example of the light path member.

Referring to FIGS. 12A and 12B, a sensor arrangement structure 1700 according to a fifth embodiment of the disclosure may include a circuit board 1720, a second IC layer 1740, a first IC layer 1760, and a light blocking member 1784. The descriptions of the circuit boards 720, 920, 1120, and 1520, the second IC layers 740, 940, 1140, and 1540, and the first IC layers 760, 960, 1160, and 1560 in FIGS. 8 to 11 may be applied to a description of the circuit board 1720, the second IC layer 1740, and the first IC layer 1760 in FIGS. 12A and 12B.

The sensor arrangement structure 1700 may further include a light path member. The light path member may be disposed in an opening region 1722. For example, a light path member 1790a (see FIG. 12A) may be disposed to extend from the opening region 1722 to the bottom surface (the −z-axis surface) of the transparent part 1702. According to an embodiment of the disclosure, the light path member may be disposed to correspond to a first light emitter 1774. For example, as described above, the first light emitter 1774 may be disposed to overlap the opening region 1722, and the light path member 1790 may be disposed to be inserted into the opening region 1722, whereby light emitted from the first light emitter 1774 may be transferred to the transparent part 1702 along the light path member 1790. According to another embodiment of the disclosure (see FIG. 12B), the transparent part 1702 may further include a hole 1703. For example, a light path member 1790b may be disposed such that one-side (−z-axis direction) part thereof is inserted into the opening region 1722 and the other-side (+z-axis direction) part thereof is inserted into the hole 1703. In another embodiment, the light path member may be disposed to surround the opening region 1722 above the circuit board 1720 without being inserted into the opening region 1722. Furthermore, the light path member, a second light emitter 1764, and/or the first IC layer 1760 may be disposed to overlap a compartment region 1785 in the horizontal direction (the x-axis direction).

In the embodiments illustrated in FIGS. 12A and 12B, the description of the elements in FIG. 11 may be applied to a second sensor module 1761 including the second light emitter 1764 (including a (2-1)th light emitter 1764a and a (2-2)the light emitter 1764b) and a second light receiver (1762), a first sensor module 1710 including the first light emitter 1774 and a first light receiver 1772), and the light blocking member 1784 including a first light blocking member 1784a and a second light blocking member 1784b. Therefore, a redundant description will be omitted.

Figure 13A:
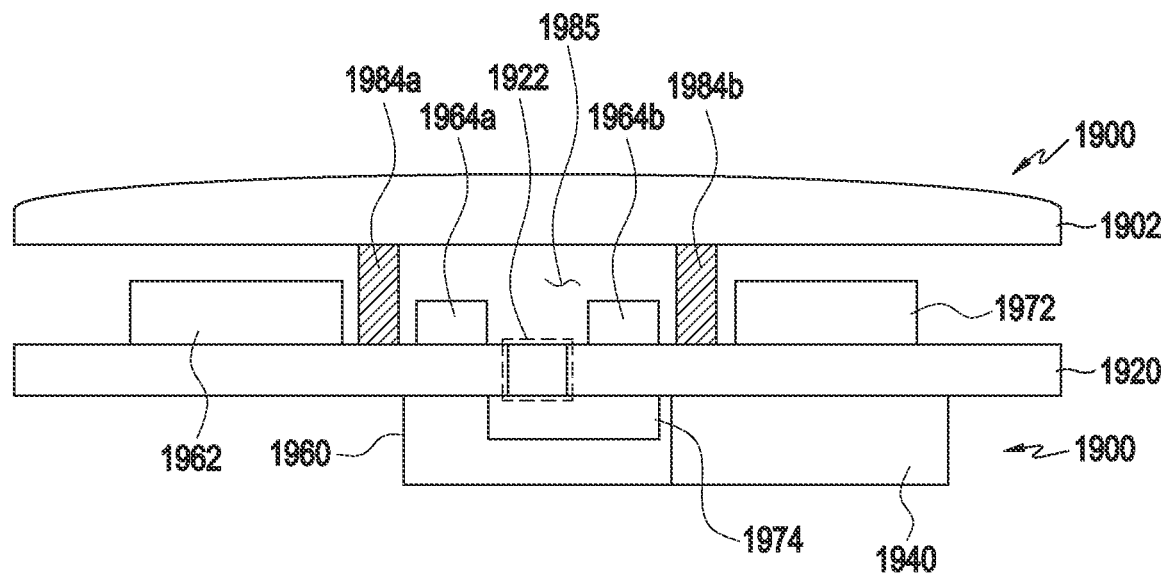
FIGS. 13A and 13B show implementation examples of a sensor arrangement structure according to various embodiment of the disclosure.
Figure 13B:
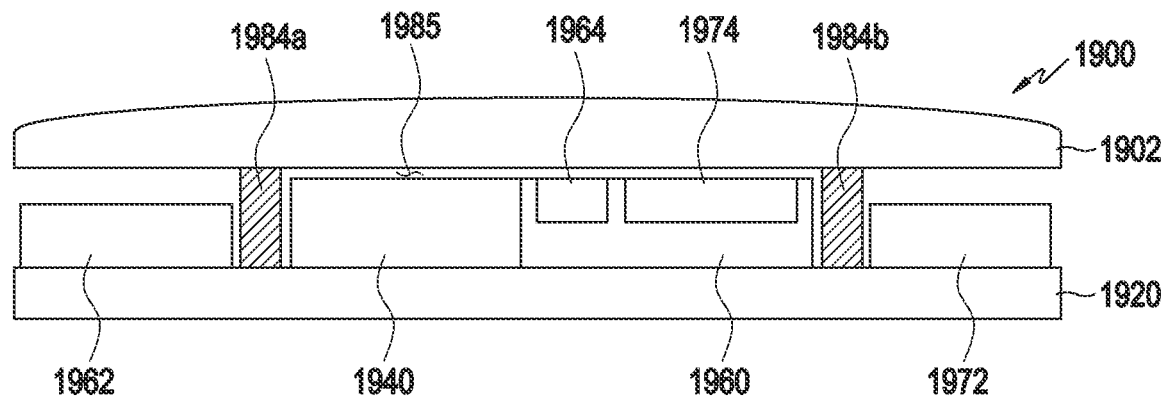
Figure 13B:
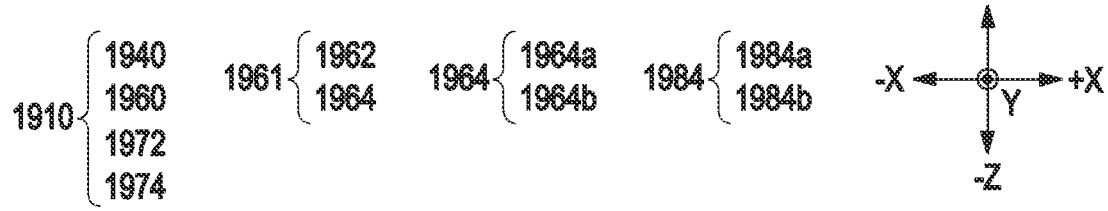

FIGS. 13A and 13B show implementation examples of a sensor arrangement structure 1900 according to various embodiments of the disclosure. FIG. 13A shows an implementation example in which a first IC layer is disposed beneath of a circuit board. FIG. 13B shows an implementation example in which a first IC layer on a circuit substrate.

Referring to FIGS. 13A and 13B, the descriptions of the circuit boards 720, 920, 1120, 1520, and 1729, the second IC layers 740, 940, 1140, 1540, and 1740, and the first IC layers 760, 960, 1160, 1560, and 1740 in FIGS. 8, 9, 10A, 10B, 11, 12A, and 12B may be applied to a description of a circuit board 1920, a second IC layer 1940, and the first IC layer 1960 in FIGS. 13A and 13B. Furthermore, in the embodiments illustrated in FIGS. 13A and 13B, the descriptions of the elements in FIGS. 11, 12A, and 12B may be applied to a second sensor module 1961 including a second light emitter 1964 (including a (2-1) light emitter 1964a and a (2-2) light emitter 1964b) and a second light receiver 1962, a first sensor module 1910 including a first light emitter 1974 and a first light receiver 1972, a light blocking member 1984 including a first light blocking member 1984a and a second light blocking member 1984b, and a transparent part 1902. Therefore, a redundant description will be emitted.

Referring to FIGS. 13A and 13B, the first IC layer 1960 and the second IC layer 1940 may be disposed adjacent to each other in the horizontal direction (the x-axis direction).

According to an embodiment of the disclosure (referring to FIG. 13A), the first IC layer 1960 and the second IC layer 1940 may be disposed adjacent to each other in the horizontal direction on the bottom surface (the −z-axis surface) of circuit board 1920. The first IC layer 1960 and the second IC layer 1940 may be disposed to be in contact with each other for space efficiency. Alternatively, the first IC layer 1960 and the second IC layer 1940 may be disposed to be spaced a predetermined interval apart from each other.

According to another embodiment of the disclosure (referring to FIG. 13B), the first IC layer 1960 and the second IC layer 1940 may be disposed adjacent to each other on the top surface (the +z-axis surface) of the circuit board 1920. The light blocking member 1984 may be disposed around the first IC layer 1960 and the second IC layer 1940. For example, the first light blocking member 1984a and the second light blocking member 1984b may be disposed at both sides of the first IC layer 1960 and the second IC layer 1940. In another example, the first IC layer 1960 and the second IC layer 1940 may be disposed in a compartment region 1985 formed between the first light blocking member 1984a and the second light blocking member 1984b.

According to an embodiment of the disclosure a wearable device includes: a housing (e.g., the housing 601 in FIG. 7) including a transparent part (e.g., the transparent part 602 in FIG. 7); a circuit board (e.g., the circuit board 720 in FIG. 8) disposed in the housing and including a first surface and a second surface opposite to the first surface; a first IC layer (e.g., the first IC layer 760 in FIG. 8) disposed adjacent to the circuit board; a first sensor module (e.g., the first sensor module 710 in FIG. 8), at least a part of which is disposed in the first IC layer; a second sensor module (e.g., the second sensor module 761 in FIG. 8) disposed adjacent to the first sensor module; and a second IC layer (e.g., the second IC layer 740 in FIG. 8) electrically connected to the first IC layer and the circuit board, and including a processor configured to process data acquired by the first sensor module and the second sensor module, wherein the circuit board, the first IC layer, and the second IC layer are stacked and disposed in a direction perpendicular to the first surface or the second surface of the circuit board.

The first sensor module may be a PPG sensor and the second sensor module may be a spectral sensor.

The first sensor module may include a first light emitter (e.g., the first light emitter 774 in FIG. 8) and a first light receiver (e.g., the first light receiver 772 in FIG. 8), and the second sensor module may include a second light emitter (e.g., the second light emitter 764 in FIG. 8) and a second light receiver (e.g., the second light receiver 762 in FIG. 8).

The first light receiver and the second light receiver may be disposed on both peripheries of the first IC layer, respectively, and the first light emitter and the second light emitter may be disposed between the first light receiver and the second light receiver.

The wearable device may further include a light transfer member (e.g., the transfer member 980 in FIG. 9) which is disposed on the first IC layer and includes at least one light blocking region (e.g., the light blocking region 984 in FIG. 9) and multiple light-transmitting regions (e.g., the light-transmitting region 982 in FIG. 9) divided by the light blocking region.

The multiple light-transmitting regions may include a first light-transmitting region and a second light-transmitting region, formed in a peripheral region of the light transfer member, and a third light-transmitting region may be formed between the first light-transmitting region and the second light-transmitting region, the first light receiver and the second light receiver may be disposed to overlap the first light-transmitting region and the second light-transmitting region, respectively, and the first light emitter and the second light emitter may be disposed to overlap the third light-transmitting region.

The first light receiver and the second light receiver may be disposed on the circuit board, and at least one of the first light emitter or the second light emitter may be disposed in the first IC layer.

The wearable device may further include a light blocking member (e.g., the light blocking member 1184 in FIGS. 10A and 10B) which includes a first member (e.g., the first light blocking member 1184a in FIGS. 10A and 10B) and a second member (e.g., the second light blocking member 1184b in FIGS. 10A and 10B) formed as partition walls, and includes a compartment region (e.g., the compartment region 1185 in FIGS. 10A and 10B) between the first member and the second member.

The first IC layer and the second IC layer may be disposed in the compartment region.

The first light receiver and the second light receiver may be disposed outside the compartment region, and the first light emitter and the second light emitter may be disposed in the compartment region.

The circuit board may further include an opening region (e.g., the opening region 1522 in FIG. 11), the first light emitter may be disposed on the first surface of the circuit board, and the second light emitter may be disposed on the second surface of the circuit board so as to at least partially overlap the opening region.

The second light emitter may be disposed on the first IC layer, and the first IC layer and the second IC layer may be stacked and disposed on the second surface of the circuit board.

The wearable device may further include a light path member (e.g., the light path member 1790 in FIGS. 12A and 12B), wherein the light path member may be disposed in the opening region so as to provide a transfer path for light emitted from the second light emitter.

According to an embodiment of the disclosure, a wearable device may include a housing (e.g., the housing 601 in FIG. 7) including a transparent part (e.g., the transparent part 602 in FIG. 8); a circuit board (e.g., the circuit board 720 in FIG. 8) which is disposed in the housing, and includes a first surface and a second surface opposite to the first surface; a first IC layer (e.g., the first IC layer 760 in FIG. 8) disposed on the circuit board, the first IC layer including a first sensor module (e.g., the first sensor module 710 in FIG. 8) and a second sensor module (e.g., the second sensor module 761 in FIG. 8) disposed adjacent to the first sensor module; a second IC layer (e.g., the second IC layer 740 in FIG. 8) electrically connected to the first IC layer and the circuit board, and including a processor configured to process data acquired by the first sensor module and the second sensor module, wherein the first IC layer and the second IC layer are disposed adjacent to each other on the first surface or the second surface in a direction parallel to the longitudinal direction of the first surface or the second surface.

The first sensor module may include a first light emitter (e.g., the first light emitter 774 in FIG. 8) and a first light receiver (e.g., the first light receiver 772 in FIG. 8), and the second sensor module may include a second light emitter (e.g., the second light emitter 764 in FIG. 8) and a second light receiver (e.g., the second light receiver 762 in FIG. 8).

The first light receiver and the second light receiver may be disposed on the circuit board, and one of the first light emitter or the second light emitter may be disposed in the first IC layer.

The wearable device may further include a light blocking member (e.g., the light blocking member 1184 in FIGS. 10A and 10B) which includes a first member (e.g., the first light blocking member 1184*a* in FIGS. 10A and 10B) and a second member (e.g., the second light blocking member 1184*b* in FIGS. 10A and 10B), formed as partition walls, and may include a compartment region (e.g., the compartment region 1185 in FIGS. 10A and 10B) between the first member and the second member.

The first IC layer and the second IC layer may be disposed in the compartment region.

The first light receiver and the second light receiver may be disposed outside the compartment region, and the first light emitter and the second light emitter may be disposed in the compartment region.

The first sensor module may be a spectral sensor, and the second sensor module may be a PPG sensor.

The circuit board may include an opening through which light is able to pass.

The first light emitter may overlap the opening.

At least a portion of the second IC layer may contact a portion of the first IC layer.

The first IC layer may be spaced apart from the second IC layer by a predetermined distance.

According to an embodiment of the disclosure a wearable device may include a housing (e.g., the housing 601 in FIG. 7) including a transparent part (e.g., the transparent part 602 in FIG. 7); a circuit board (the circuit board 720 in FIG. 8) which is disposed in the housing and includes a first surface facing the transparent part and a second surface opposite to the first surface; a processor connected to the circuit board; a first sensor module (e.g., the first sensor module 710 in FIG. 8) including a first light emitter (e.g., the first light emitter 774 in FIG. 8) configured to emit light toward the transparent part, a first light receiver (e.g., the first light receiver 772 in FIG. 8) configured to receive light incident from the transparent part, a first IC layer (e.g., the first IC layer 760 in FIG. 8) which includes a modulator electrically connected to the first light emitter and the first light receiver so as to modulate light incident on the first light receiver and in which at least one of the first light emitter or the first light receiver is disposed, and a second IC layer (e.g., the second IC layer 740 in FIG. 8) electrically connects the first IC layer to the processor and disposed on the first surface or the second surface of the circuit board; and a second sensor module (e.g., the second sensor module 761 in FIG. 8) spaced apart from the first sensor module, wherein the first IC layer is disposed between the circuit board and the transparent part, and the second IC layer is disposed between the circuit board and the first IC layer.

The electronic device including a binding member of the disclosure, described above, is not limited by the above-mentioned embodiments and drawings, and it will be apparent to those skilled in the art, to which the disclosure belongs, that various substitutions, modifications, and changes are possible within the technical scope of the disclosure.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. A wearable device comprising:
   a housing comprising a transparent part;
   a circuit board which is disposed in the housing and comprising:
     a first surface facing the transparent part, and
     a second surface opposite to the first surface;
   a processor connected to the circuit board;
   a first sensor module comprising:
     a first light emitter configured to emit light toward the transparent part,
     a first light receiver configured to receive light from the transparent part,
     a first integrated circuit (IC) layer comprising a modulator electrically connected to the first light emitter and the first light receiver so as to modulate light received on the first light receiver and in which at least one of the first light emitter or the first light receiver is disposed, and
     a second IC layer electrically connecting the first IC layer to the processor and disposed on the first surface or the second surface of the circuit board; and
   a second sensor module comprising a second light emitter and a second light receiver, wherein the first light receiver and the second light receiver are respectively disposed at opposite peripheries of the first IC layer,
wherein the first light emitter and the second light emitter are disposed between the first light receiver and the second light receiver, and
wherein the circuit board, the second IC layer, and the first IC layer are sequentially stacked in a direction perpendicular to the first surface or the second surface.

2. The wearable device of claim 1, further comprising:
a light transfer member which is disposed on the first IC layer, and comprising:
   at least one light blocking region, and
   multiple light-transmitting regions divided by the light blocking region.

3. The wearable device of claim 2,
wherein the multiple light-transmitting regions comprise:
   a first light-transmitting region and a second light-transmitting region, formed in a peripheral region of the light transfer member, and
   a third light-transmitting region formed between the first light- transmitting region and the second light-transmitting region,
wherein the first light receiver and the second light receiver are disposed to overlap the first light-transmitting region and the second light-transmitting region, respectively, and
wherein the first light emitter and the second light emitter are disposed to overlap the third light-transmitting region.

4. The wearable device of claim 1,
wherein the first light receiver and the second light receiver are disposed on the circuit board, and
wherein at least one of the first light emitter or the second light emitter is disposed in the first IC layer.

5. The wearable device of claim 1, further comprising:
a light blocking member comprising:
   a first member and a second member formed as partition walls, and
   a compartment region between the first member and the second member.

6. The wearable device of claim 5, wherein the first IC layer and the second IC layer are disposed in the compartment region.

7. The wearable device of claim 5,
wherein the first light receiver and the second light receiver are disposed outside the compartment region, and
wherein the first light emitter and the second light emitter are disposed in the compartment region.

8. The wearable device of claim 1,
wherein the circuit board further comprises an opening region,
wherein the first light emitter is disposed on the first surface of the circuit board, and
wherein the second light emitter is disposed on the second surface of the circuit board so as to at least partially overlap the opening region.

9. The wearable device of claim 8,
wherein the first light emitter is disposed on the first IC layer, and
wherein the first IC layer and the second IC layer are stacked and disposed on the second surface of the circuit board.

10. The wearable device of claim 8, further comprising:
a light path member,
wherein the light path member is disposed in the opening region so as to provide a transfer path for light emitted from the first light emitter.

11. The wearable device of claim 1, wherein the first sensor module and the second sensor module are different types of senor modules.

12. A wearable device comprising:
a housing comprising a transparent part;
a circuit board which is disposed in the housing, and comprising:
   a first surface facing the transparent part, and
   a second surface opposite to the first surface;
a processor connected to the circuit board;
a first sensor module comprising:
   a first light emitter configured to emit light toward the transparent part,
   a first light receiver configured to receive light from the transparent part,
   a first integrated circuit (IC) layer comprising a modulator electrically connected to the first light emitter and the first light receiver so as to modulate light received on the first light receiver and in which at least one of the first light emitter or the first light receiver is disposed, and
   a second IC layer electrically connecting the first IC layer to the processor and disposed on the first surface or the second surface of the circuit board;
a second sensor module comprising a second light emitter and a second light receiver; and
a light blocking member comprising:
   a first member and a second member formed as partition walls, and
   a compartment region between the first member and the second member,
wherein the first light receiver and the second light receiver are disposed outside the compartment region,
wherein the first light emitter and the second light emitter are disposed in the compartment region, and
wherein the first IC layer and the second IC layer are disposed parallel to each other on one of the first surface or the second surface of the circuit board.

13. The wearable device of claim 12,
wherein the first light receiver and the second light receiver are disposed on the first surface of the circuit board, and
wherein one of the first light emitter or the second light emitter is disposed in the first IC layer.

14. The wearable device of claim 12, wherein the first IC layer and the second IC layer are disposed in the compartment region.

15. The wearable device of claim 12, wherein the first sensor module and the second sensor module are different types of senor modules.

16. A wearable device comprising:
a housing comprising a transparent part;
a circuit board which is disposed in the housing and comprising:
   a first surface facing the transparent part, and
   a second surface opposite to the first surface;
a processor connected to the circuit board;
a first sensor module comprising:
   a first light emitter configured to emit light toward the transparent part,
   a first light receiver configured to receive light from the transparent part; part,
   a first integrated circuit (IC) layer comprising a modulator electrically connected to the first light emitter and the first light receiver so as to modulate light received on the first light receiver and in which at least one of the first light emitter or the first light receiver is disposed, and a second IC layer electrically connecting the first IC layer to the processor and disposed on the first surface or the second surface of the circuit board; and a second sensor module spaced apart from the first sensor module, and comprising a second light emitter and a second light receiver, wherein the first IC layer is disposed between the circuit board and the transparent part, wherein the second IC layer is disposed between the circuit board and the first IC layer, wherein the first light emitter, the first light receiver, the second light emitter, and the second light receiver are disposed in the first IC layer provided as a single layer, and wherein surfaces of the first light emitter, the first light receiver, the second light emitter, and the second light receiver are in a same plane as a surface of the first IC layer.

17. The wearable device of claim 16, wherein the first sensor module and the second sensor module are different types of senor modules.

* * * * *